(12) United States Patent
Nagaoka

(10) Patent No.: US 7,494,657 B2
(45) Date of Patent: Feb. 24, 2009

(54) INHIBITOR OF HEPATITIS B AND HIV ACTIVITY

(76) Inventor: Hitoshi Nagaoka, 22-13, Kotobuki 2-chome, Abiko-shi, Chiba 270-11 (JP)

( * ) Notice: Subject to any disclaimer, the term of this patent is extended or adjusted under 35 U.S.C. 154(b) by 978 days.

(21) Appl. No.: 10/644,221

(22) Filed: Aug. 19, 2003

(65) Prior Publication Data

US 2004/0038330 A1 Feb. 26, 2004

Related U.S. Application Data

(60) Division of application No. 08/519,293, filed on Aug. 25, 1995, now abandoned, which is a continuation of application No. 08/257,355, filed on Jun. 9, 1994, now abandoned.

(30) Foreign Application Priority Data

Dec. 17, 1993 (JP) ............................. 1993-317564

(51) Int. Cl.
*A61K 35/84* (2006.01)
*A23L 2/38* (2006.01)

(52) U.S. Cl. ................................. 424/195.15

(58) Field of Classification Search ................ None
See application file for complete search history.

(56) References Cited

U.S. PATENT DOCUMENTS

| 4,461,760 A | 7/1984 | Sugano et al. |
| 4,629,627 A | 12/1986 | Iizuka |

FOREIGN PATENT DOCUMENTS

| JP | 6023826 | * | 6/1985 |
| JP | 60-149369 A | | 8/1985 |
| JP | 60-149528 A | | 8/1985 |
| JP | 01-312980 A | | 12/1989 |
| JP | 46171 | | 2/1992 |
| JP | 435149 | | 6/1992 |

OTHER PUBLICATIONS http://en.wikipedia.org/wiki/List_of_viruses.*
Amagase H. Treatment of hepatitis B patients with Lentinus edodes mycelia. In: New Trends in Peptic Ulcer and Chronic Hepatitis, Part II, Chronic Hepatitis. Princeton: Exerpta Medica 1987;316-21.*
Pauwels, R., Antiviral Research, 71 (2006), pp. 77-89.*
Tetsuo Taguchi et al., Biotherapy, vol. 2, No. 3 (1988) pp. 509-521.
Harumi Suzuki et al., *Inhibition of the Infectivity and Cytopathic Effect of Human* . . . , Biochemical and Biophysical Research Communications, vol. 160, No. 1 (1989) pp. 367-373.
Harumi Suzuki et al., *Structural Characterization of the Immunoactive and Antiviral* . . . , Agric. Biol. Chem., vol. 54, No. 2 (1990) pp. 479-487.
Yoshio Inouye et al., *In Vitro Antiviral Activity of Polyoxomolybdates* . . . , Antiviral Research, vol. 20 (1993) pp. 317, 321-322.
Johnston et al., Science, vol. 260, 1993, p. 1111.

* cited by examiner

*Primary Examiner*—Irene Marx
(74) *Attorney, Agent, or Firm*—The Webb Law Firm

(57) ABSTRACT

The inhibitor of Hepatitis B virus and HIV activity according to the present invention comprises a *Lentinus edodes* mycelium extract obtained by the steps of inoculating *Lentinus edodes* fungus in a solid culture medium comprising bagasse, then disentangling the solid culture medium containing the proliferated mycelium, adding water and at least one enzyme selected from a group consisting of cellulase, protease and glucosidase to the disentangled solid culture medium with keeping the solid culture medium at 30 to 50° C., grinding and milling the solid culture medium in the presence of the enzyme to obtain a *Lentinus edodes* mycelium extract, and then heating the extract to a temperature of not higher than 95° C. to inactivate the enzyme and sterilize the extract.

2 Claims, 1 Drawing Sheet

INHIBITOR OF HEPATITIS B AND HIV ACTIVITY

CROSS REFERENCE TO RELATED APPLICATIONS

This application is a divisional of application Ser. No. 08/519,293, filed Aug. 25, 1995, now abandoned, which is a continuation of application Ser. No. 08/257,355 filed Jun. 9, 1994, now abandoned, which, in turn, claims priority to Japanese Application No. 317564/1993, filed Dec. 17, 1993, all of which are incorporated herein by reference.

FIELD OF THE INVENTION

The present invention relates to an inhibitor of Hepatitis B virus and HIV (human immunodeficiency virus) activity, and more particularly to an inhibitor of Hepatitis B and HIV activity which is therapeutically effective for these infectious diseases and hardly brings about side effects.

BACKGROUND OF THE INVENTION

It was reported that the first deceased by HIV-infection in the world was found in Africa in 1950, and in an instant, the HIV-infected persons spread all over the world. Recently, it has been reported that a great number of persons were infected with HIV and deceased.

The therapeutic agents for the HIV-infected persons include AZT, ddI, ddC, interleukin-II, GL0223, DHCA, γ-beta-ser Interferon, alpha interferon, gamma interferon, etc.

However, these therapeutic agents have problems of serious side effects or poor efficacy, and any inhibitor or HIV activity (i.e., HIV activity inhibitor) with special efficacy has not been found yet.

On that account, the present inventor has earnestly studied to pursue an inhibitor which inhibits viral activity of Hepatitis B virus and HIV, is able to destroy said viruses and is almost free from anxiety of side effects. As a result, he has found that a specific mycelium extract prepared by a specific process inhibits the Hepatitis B and HIV activity and restrains proliferation of said virus, and he has accomplished the present invention.

Japanese Patent Publication No. 23826/1985 describes a process for preparing a healthful drink comprising the steps of inoculating *Lentinus edodes* fungus in a solid culture medium comprising bagasse, then untying (disentangling) the solid culture medium containing the proliferated mycelium in such a manner that the amount of the disentangled medium of 12-in mesh would be not more than 30% by weight, adding water and at least one enzyme selected from a group consisting of cellulase, protease and glucosidase to the disentangled solid culture medium with keeping the solid culture medium at 30 to 50° C., grinding and milling the solid culture medium in the presence of the enzyme so that the amount of the bagasse fibers of 12-in mesh is at least 70% by weight, then heating to a temperature of not higher than 95° C. to inactivate the enzyme and sterilize, and filtering the resultant suspension.

Further, Japanese Patent Applications No. 5355/1984 and No. 5356/1984 (i.e., Japanese Patent Publications No. 35149/1992 and No. 6171/1992, respectively) describe processes for preparing healthful drinks using *Fomes japonicus* fungus.

In these publications, however, there is neither description nor suggestion on that the obtained healthful drinks are effective as inhibitors against Hepatitis B virus or HIV activity.

With respect to physiologically active substances obtained from *Lentinus edodes* (Japanese edible mushroom, shiitake), some literatures have reported.

In "BIOTHERAPY," Vol. 2, No. 3, pp. 509-521 (June, 1988), Tetsuo Taguchi et al. state that lentinan obtained from *Lentinus edodes* inhibits proliferation of HIV by the use thereof in combination with the HIV therapeutic agent AZT. Further, in "Pharmaceutical Magazine," Vol. 108, No. 3, pp. 171-186 (1988), Kureo Chihara, who is a co-writer of the above thesis, reports that the main substance of polysaccharides obtained from *Lentinus edodes* is β-1,6:β-1,3-D-glucan.

Furthermore, in "BIOCHEMICAL AND BIOPHYSICAL RESEARCH COMMUNICATIONS," Vol. 160, No. 1, pp. 367-373 (1989), Harumi Suzuki et al. report that an extract of *Lentinus edodes* mycelium (LEM) has anti-HIV effect, and it is describe in "Agri. Biol. Chem.," Vol 54, No. 2, pp. 479-487 (1990) that the main substance of said extract is a water-soluble lignin contained in the LEM.

By the way, the inhibitor of HIV activity of the present invention exhibits sufficient inhibitory effect against the HIV activity in a concentration of 125 μg/ml in vitro even when it is in the unpurified state, and differs from the above-mentioned substances already reported. The activity against Hepatitis B virus is similar, and the inhibitor is also useful in treating liver cancer.

OBJECT OF THE INVENTION

The present invention is intended to solve such problems associated with the prior art techniques as described above, and it is an object of the invention to provide an inhibitor of Hepatitis B virus and HIV activity, which is able to restrain proliferation of said virus and is excellent in the safety by virtue of less anxiety of side effects.

SUMMARY OF THE INVENTION

The inhibitor of Hepatitis B virus and HIV activity according to the present invention comprises a *Lentinus edodes* mycelium extract obtained by the steps of inoculating *Lentinus edodes* fungus in a solid culture medium comprising bagasse, then disentangling the solid culture medium containing the proliferated mycelium, adding water and at least one enzyme selected from a group consisting of cellulase, protease and glucosidase to the disentangled solid culture medium with keeping the solid culture medium at 30 to 50° C., grinding and milling the solid culture medium in the presence of the enzyme to obtain a *Lentinus edodes* mycelium extract, and then heating the extract to a temperature of not higher than 95° C. to inactivate the enzyme and sterilize the extract.

The Hepatitis B virus and HIV activity inhibitor comprising the *Lentinus edodes* mycelium extract obtained by the above process inhibits viral activity of Hepatitis B virus and HIV, is able to restrain proliferation of said virus and is excellent in the safety by virtue of less anxiety of side effects. The inhibitor is also active against liver cancer.

DETAILED DESCRIPTION OF THE INVENTION

Figure 1:
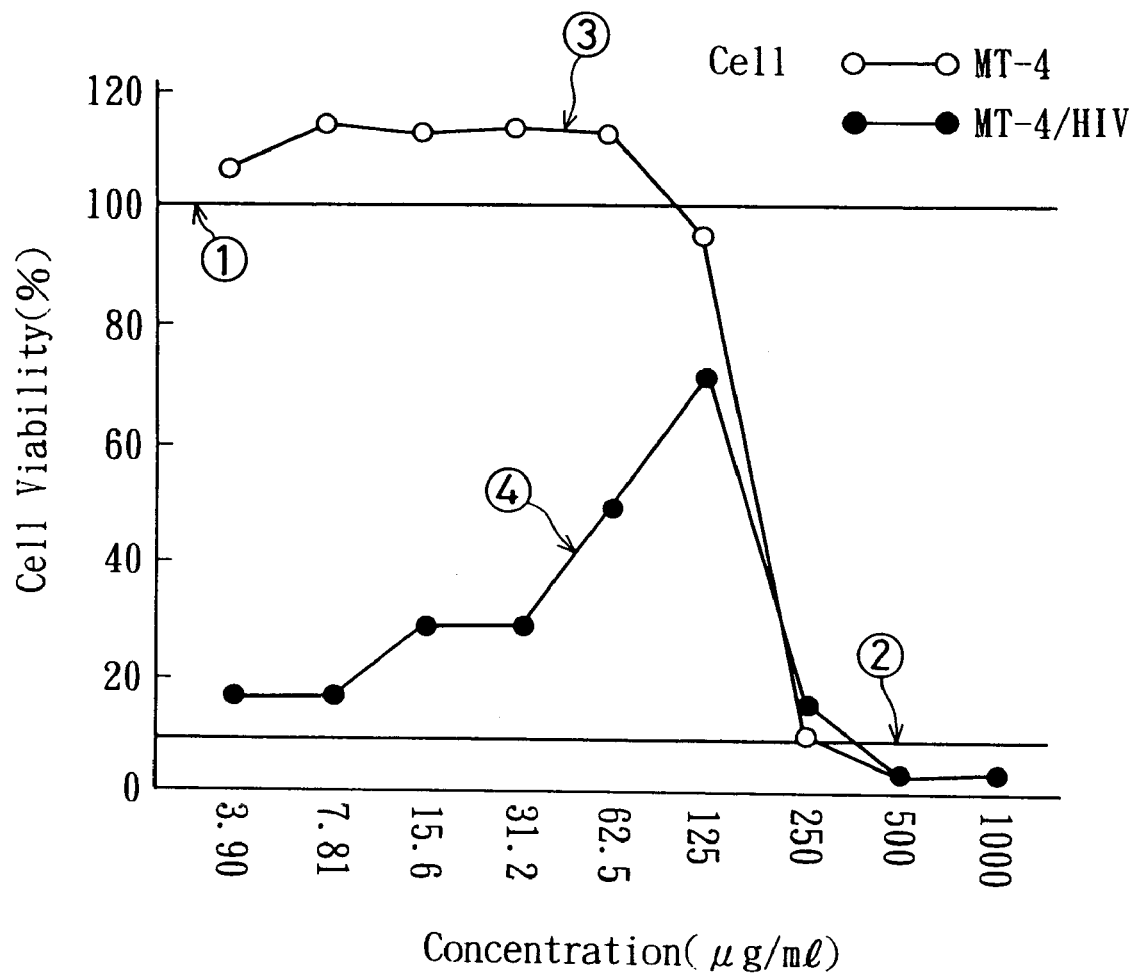
FIG. 1 graphically shows an inhibition activity of the HIV activity inhibitor of the present invention.

The inhibitor of Hepatitis B virus and HIV activity according to the present invention will be described in detail hereinafter.

The inhibitor of Hepatitis B virus and HIV activity according to the invention contains at least one extract of *Lentinus edodes* mycelium.

For preparing the extract of the *Lentinus edodes* mycelium, a solid culture medium composed of bagasse is appropriately mixed with water, preferable pure water, and then *Lentinus edodes* fungus is inoculated in the solid culture medium. This bagasse culture medium may be supplemented, if necessary, with rice bran, minerals (e.g., phosphorus, iron, germanium), peanut shell and unpolished rice.

Subsequently, the culture medium inoculated with the *Lentinus edodes* fungus is placed in a culture room which has been adjusted in the temperature, the humidity and the illuminance, to proliferate the mycelium.

The Mycelium are widespread in the solid culture medium and mushroom bodies are formed. It is desired that immediately before and after the formation of the mushroom bodies, the bagasse substrate is disentangled so that the amount of the bagasse of 12-in mesh is not more than 30% by weight. Namely, the disentangled bagasse substrate which passes through 12 mesh screen is not more than 30% by weight. The disentangling of the bagasse substrate culture medium is preferable carried out immediately before and after the formation of the mushroom bodies as described above, but it may be carried out after the mushroom bodies are relatively grown.

The solid culture medium thus disentangled is supplemented with water and at least one enzyme selected from a group consisting of cellulase, protease and glucosidase, with keeping the solid culture medium at 30 to 50° C. Of these enzymes, cellulase is preferably added The amount of the enzyme to be added is in the range of 0.5 to 5 g, preferably 1 to 3 g, per 1 kg of the solid culture medium. Water to be added is preferably pure water not containing ions such as metallic ions. The pure water is added in an amount of 1 to 10 kg, preferably 2 to 6 kg, per 1 kg of the disentangled culture medium, to give a bagasse-containing mixture.

Then, an extract of *Lentinus edodes* mycelium is taken out from the bagasse-containing mixture. For taking out the *Lentinus edodes* mycelium extract, it is desired that the solid culture medium is subjected to grinding and milling so that the amount of the bagasse fibers of 12-in mesh is not less than 70% by weight (the ground and milled solid culture medium which passes through 12 mesh screen is not less than 70% by weight), while circulating the culture medium-containing mixture by means of, for example, a speed change gear pump.

The grinding and milling of the bagasse-containing mixture may be conducted with keeping the temperature of said mixture at 30 to 50° C., or may be conducted with slowly elevating the temperature of said mixture over the above temperature. Preferably, the grinding and milling are conducted with slowly elevating the temperature. If air of room temperature is injected into the bagasse-containing mixture at the time when the water temperature becomes not lower than 60° C., preferably not lower than 70° C., the air bubbles are abruptly heated and ruptured so as to apply impact to the bagasse fibers, whereby extraction of the effective component can be efficiently carried out.

The bagasse-containing mixture thus treated is then further heated to a temperature of not higher than 95° C., preferably about 75 to 90° C., and kept at the same temperature for several tens of minutes to inactivate the enzyme in the mixture and sterilize said mixture. Thus, an extract of *Lentinus edodes* mycelium is obtained.

If desired, the extract of *Lentinus edodes* mycelium thus obtained may be filtered through a filter cloth of 50 to 120-in mesh, preferably about 60 to 100-in mesh.

The extract of *Lentinus edodes* mycelium as obtained above can be used as its concentrate, or can be used in the form of a powder obtained by freeze-drying the extract.

Such Hepatitis B virus or HIV activity inhibitor may be used by oral administration in various forms such as granule, liquid, tablet and capsule. It is also possible to develop an injection liquid of said inhibitor, which acts on the infected persons. The Hepatitis B/HIV activity inhibitor containing the above-mentioned mycelium extract can be administered to the Hepatitis B- or HIV-infected person without being diluted, but it can be administered by appropriately diluting it with, for example, purified water or alcohol.

When the Hepatitis B/HIV activity inhibitor of the invention comprising the extract of *Lentinus edodes* mycelium is administered to the infected person as described above, the viral activity is remarkably weakened and proliferation of said virus can be inhibited. In addition, the cells weakened by the HIV-infection or Hepatitis B infection can be revived and can live for a long period of time.

The reason why administration of the Hepatitis B/HIV activity inhibitor of the invention comprising the extract of *Lentinus edodes* mycelium to the infected person makes it possible to weaken the viral activity, to inhibit proliferation of said virus and to activate the human cells having been infected with the viruses as described above is assumed as follows, although there is no intention to be bound thereby.

According to the studies of the present inventor, it is thought that the Hepatitis B/HIV activity inhibitor comprising the extract of *Lentinus edodes* mycelium contains a large number of effective components extracted from the *Lentinus edodes* mycelium and extracted from the solid culture medium cultured with the *Lentinus edodes* mycelium in the mixed state, and these effective components (unidentified) possess the anti-HIV/anti-Hepatitis B activity.

This is assumable from the fact that the effective components extracted from only the *Lentinus edodes* mycelium hardly show inhibitory activity against HIV or Hepatitis B and also the effective components extracted from only the solid culture medium (bagasse) hardly show inhibitory activity against HIV or Hepatitis B.

The *Lentinus edodes* mycelium extract of the present invention is also effective to treat cancer of the liver, as reported above.

EFFECT OF THE INVENTION

According to the present invention, there is provided an inhibitor of HIV or Hepatitis B activity which is able to inhibit viral activity of HIV or Hepatitis B or proliferation of said viruses, is able to promote the activities of the human cells having been infected with HIV or Hepatitis B, and is excellent in the safety by virtue of less anxiety of side effects.

EXAMPLE

The present invention is described below in more detail with reference to examples, but it should be construed that the invention is in no way limited to those examples.

Preparation Example 1

[Preparation of an HIV/Hepatitis B Activity Inhibitor Comprising a *Lentinus edodes* Mycelium Extract.]

Pure water was appropriately added to a solid culture medium composed of 90 parts by weight of bagasse and 10 parts by weight of rice bran. Then, *Lentinus edodes* fungus was inoculated in the solid culture medium. The thus treated solid culture medium was placed in a culture room having been adjusted in the temperature and the humidity, to proliferate *Lentinus edodes* mycelium. After the mycelium were proliferated and widespread in the solid culture medium, cellulose of the bagasse substrate was disentangled so that the amount of the bagasse fibers of 12-in mesh was 24% by weight. To 1.0 kg of the culture medium thus disentangled were added 3.5 liters of pure water and 2.0 g of purified cellulase with keeping the solid culture medium at 40° C., to give a bagasse-containing mixture.

Subsequently, while circulating the culture medium-containing mixture by means of a speed change gear pump, the mixture was subjected to grinding and milling at the gear part of the pump for a period of about 200 minutes so that the amount of the bagasse fibers of 12-in mesh was about 80% by weight. The grinding and milling of the bagasse-containing mixture were carried out with slowly elevating the temperature of the mixture.

Thereafter, the bagasse-containing mixture was further heated to 90° C., and allowed to stand for 30 minutes at the same temperature.

By the heating to 90° C., inactivation of the enzyme and sterilization of the mixture were performed.

The culture medium-containing mixture thus obtained was filtered through a filter cloth of 60-in mesh to obtain a *Lentinus edodes* mycelium extract containing fine suspended matter.

Test Examples 1-10

With respect to the HIV activity comprising the *Lentinus edodes* mycelium extract obtained in the above-mentioned Preparation Example 1, the anti-HIV effect was measured in accordance with the method described in "Antiviral Research," Vol. 20, pp. 317-331, (1993).

In detail, human T4 lymph cells MT-4, which were obtained by modifying human helper T cells with an adult T cell leukemia virus, were used as target cells. The MT-4 cells ($10^5$/ml) were infected with HIV (HIV-1 type RF stock, $2\times10^3$ $TCD_{50}$/ml) at 37° C. for 1 hour.

The MT-4 cells thus infected with HIV (infection multiplicity: 0.02) were then washed with a fresh culture medium to remove non-absorbed viruses. Thereafter, the number of the cells was adjusted to be $5\times10^4$ cells/ml, and the cells were portioned into each well of a 96-well microplate, in an amount of 100 µl, respectively.

Subsequently, to each of the microplate wells containing the HIV-infected MT-4 cells was added 100 µl of a culture medium wherein the HIV activity inhibitor having a concentration of twice as much as the final concentration was dissolved, to conduct culturing at 37° C. for 5 to 6 days.

On the last day in the culturing, to each of the wells of the microplate was added MTT [3-(4,5-dimethylthiazol-2-yl)-2,5-diphenyl tetrazolium bromide], followed by further culturing for another 4 hours. Then, the density of a formazan dye produced was subjected to colorimetry by measuring the absorbance at 595 nm.

The results are set forth in Table 1.

In Table 1, also set forth is the density (absorbance) of a formazan dye which was produced in the same manner as described above except that the HIV activity inhibitor obtained in Preparation Example 1 was added to target cells MT-4 having been infected with no HIV.

The activity (viability) indication (%) shown in Table 1 was determined as follows. To 100 µl of the culture medium containing the target cells MT-4 was added 100 µl of a culture medium containing no HIV activity inhibitor (concentration of HIV activity inhibitor=0), to culture the target cells MT-4. After culturing of the target cells MT-4, the color density was determined by means of colorimetry at 595 nm, and the absorbance in this case was set to 100 (Test No. 1). Further, the HIV activity inhibitors with various concentrations were used to measure absorbances in the same manner as described above. A ratio of each absorbance thus obtained to the above absorbance was indicated by percentage (%), and this value was taken as indication of cell activity (cell viability). For example, the absorbance in Test Example 2 is 1.122, and the absorbance in Test Example 1 is 1.056, and therefore the cell viability (%) of Test Example 2=1.122/1.056≅106.3%.

TABLE 1

| Test No. | Concentration (µg/ml) | MT-4 Absorbance | Viability | MT-4/HIV Absorbance | Viability |
|---|---|---|---|---|---|
| 1 | Control | 1.056 | 100.0 | 0.089 | 8.4 |
| 2 | 3.9063 | 1.122 | 106.3 | 0.174 | 16.5 |
| 3 | 7.8125 | 1.207 | 114.3 | 0.175 | 16.6 |
| 4 | 15.6250 | 1.191 | 112.8 | 0.310 | 29.4 |
| 5 | 31.2500 | 1.196 | 113.3 | 0.304 | 28.8 |
| 6 | 62.5000 | 1.192 | 112.9 | 0.515 | 48.8 |
| 7 | 125.0000 | 0.991 | 93.8 | 0.755 | 71.5 |
| 8 | 250.0000 | 0.105 | 9.9 | 0.155 | 14.7 |
| 9 | 500.0000 | 0.034 | 3.2 | 0.032 | 3.0 |
| 10 | 1,000.0000 | 0.040 | 3.8 | 0.046 | 4.4 |

FIG. 1 graphically shows the results set forth in Table 1.

As is evident from the results set forth in Table 1 or FIG. 1, when the concentration of the HIV activity inhibitor exceeds 125 µg/ml, the viability of the MT-4 cells is reduced because of the influence originating from the HIV activity inhibitor, even if the cells are not infected with HIV. However, in the concentrations of not higher than the above concentration, with increase of the concentration of the HIV activity inhibitor, the viability of the HIV-infected MT-4 cells increases owing to the anti-AIDS viral effect of the HIV activity inhibitor. In particular, when the concentration of the HIV activity inhibitor is 125 µg/ml, the viability of the HIV-infected MT-4 cells is 71.5%.

The invention claimed is:

1. A method for treating a human infected with human immunodeficiency virus (HIV), comprising:
   (a) inoculating *Lentinus edodes* fungus in a solid culture medium comprising 90 parts by weight of bagasse and 10 parts by weight of rice bran to yield proliferated mycelium;
   (b) disentangling the solid culture medium containing the proliferated mycelium so that the amount of the bagasse of 12-in mesh is not more than 30% by weight and adding thereto 1 to 10 kg of water and 0.5 to 5 g of at least one enzyme selected from the group consisting of cellulase, protease and glucosidase based on 1 kg of the disentangled solid culture medium, while keeping the solid culture medium at 30 to 50° C., to give a bagasse-containing mixture;
   (c) grinding and milling the bagasse-containing mixture so that the amount of the bagasse of 12-in mesh is not less than 70% by weight;
   (d) heating the ground and milled bagasse-containing mixture to a temperature of 75 to 95° C. to inactivate the enzyme;
   (e) filtering the resultant mixture through a filter cloth of 50 to 120-in mesh to thereby obtain a purified, concentrated pharmaceutical *Lentinus edodes* mycelium extract; and
   (f) administering orally at least one effective dose of said purified, concentrated extract to said human, wherein said extract weakens HIV activity and inhibits HIV proliferation in said human.

2. The method according to claim 1 wherein the enzyme is cellulase.

* * * * *